United States Patent
O'Brien, II et al.

(10) Patent No.: US 12,226,134 B2
(45) Date of Patent: Feb. 18, 2025

(54) RIGID STERNAL FIXATION

(71) Applicant: Zimmer Biomet CMF and Thoracic, LLC, Jacksonville, FL (US)

(72) Inventors: Todd Shay O'Brien, II, Jacksonville, FL (US); Ely Lucas Knowles, Jacksonville, FL (US); Max Holland Billard, Jacksonville, FL (US); Adam Webster Hausman, Jacksonville, FL (US); Saddy Rodolfo Garcia, St. Augustine, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 106 days.

(21) Appl. No.: 17/592,142

(22) Filed: Feb. 3, 2022

(65) Prior Publication Data
US 2022/0249144 A1 Aug. 11, 2022

Related U.S. Application Data (60) Provisional application No. 63/147,409, filed on Feb. 9, 2021.

(51) Int. Cl.
*A61B 17/82* (2006.01)
*A61B 17/17* (2006.01)
(Continued)

(52) U.S. Cl.
CPC ........ *A61B 17/823* (2013.01); *A61B 17/1789* (2016.11); *A61B 17/8861* (2013.01); *A61B 2017/00407* (2013.01)

(58) Field of Classification Search
CPC ..... A61B 17/82; A61B 17/823; A61B 17/826; A61B 17/8861; A61B 17/1789;
(Continued)

(56) References Cited

U.S. PATENT DOCUMENTS 3,739,429 A * 6/1973 Kohke ............... B65D 63/1054
24/16 PB
4,910,831 A * 3/1990 Bingold ................. E05B 75/00
292/307 R
(Continued)

FOREIGN PATENT DOCUMENTS

JP 2024505722 A 2/2024
JP 7499422 B2 6/2024
(Continued)

OTHER PUBLICATIONS

"International Application Serial No. PCT/US2022/015097, International Search Report mailed May 24, 2022", 7 pgs.
(Continued)

*Primary Examiner* — Matthew J Lawson
(74) *Attorney, Agent, or Firm* — SCHWEGMAN LUNDBERG & WOESSNER, P.A.

(57) ABSTRACT

An anchor assembly, for securing a first portion and a second portion of a separated sternum, can include a lock, an anchor, and a cerclage. The anchor can include a body locatable between the first portion and the second portion of the sternum, where the body can define an end portion. The anchor can include a collar connected to the body and extending outward from the end portion of the body. The collar can engage an outer surface of the sternum to limit movement of the body beyond the outer surface of the sternum. The cerclage can be connected to and can extend from the anchor. The cerclage can be configured to at least partially surround the first portion and the second portion of the separated sternum.

12 Claims, 10 Drawing Sheets

(51) Int. Cl.
*A61B 17/88* (2006.01)
*A61B 17/00* (2006.01)

(58) Field of Classification Search
CPC .............. A61B 17/1792; A61B 17/842; B65D 2563/00; B65D 2563/10; B65D 2563/101; B65D 2563/102; B65D 2563/103; B65D 2563/104; B65D 2563/105; B65D 2563/106; B65D 2563/107; B65D 2563/108
USPC ........................................................ 24/16 PB
See application file for complete search history.

(56) References Cited

U.S. PATENT DOCUMENTS

| | | | |
|---|---|---|---|
| 5,330,489 A | 7/1994 | Green et al. | |
| 5,356,417 A | 10/1994 | Golds | |
| 5,462,542 A | 10/1995 | Alesi, Jr. | |
| 5,571,105 A | 11/1996 | Gundolf | |
| 5,802,888 A * | 9/1998 | Parsons .................. | E05B 75/00 24/16 PB |
| 6,045,572 A | 4/2000 | Johnson et al. | |
| 6,196,033 B1 * | 3/2001 | Dowdle .................. | E05B 75/00 24/16 PB |
| 7,437,804 B1 * | 10/2008 | Geiger .................... | F16L 3/237 248/74.3 |
| 8,460,345 B2 | 6/2013 | Steger et al. | |
| 8,685,027 B2 * | 4/2014 | Chico Roca ....... | A61B 17/8061 606/70 |
| 9,585,705 B2 | 3/2017 | Koch et al. | |
| 9,643,764 B1 * | 5/2017 | Huang ............... | B65D 63/1072 |
| 10,179,011 B2 | 1/2019 | Garfein et al. | |
| 10,329,062 B2 * | 6/2019 | Lee .................... | B65D 63/1063 |
| 10,745,182 B1 * | 8/2020 | Reznar .............. | B65D 63/1072 |
| 2002/0104196 A1 * | 8/2002 | Geiger .............. | B65D 63/1072 24/16 PB |
| 2003/0153947 A1 | 8/2003 | Koseki | |
| 2005/0076478 A1 * | 4/2005 | Miyazaki ........... | B65D 63/1063 24/16 PB |
| 2005/0240189 A1 | 10/2005 | Rousseau et al. | |
| 2010/0179600 A1 | 7/2010 | Steger et al. | |
| 2010/0229350 A1 * | 9/2010 | Kostal ..................... | E05B 75/00 24/16 PB |
| 2011/0022050 A1 * | 1/2011 | McClellan ........... | A61B 17/823 606/228 |
| 2011/0106153 A1 | 5/2011 | Stone et al. | |
| 2011/0295257 A1 | 12/2011 | Mcclellan et al. | |
| 2012/0041441 A1 | 2/2012 | Bernstein et al. | |
| 2012/0197257 A1 | 8/2012 | Knueppel | |
| 2013/0261625 A1 * | 10/2013 | Koch ................. | A61B 17/1691 606/74 |
| 2014/0088655 A1 | 3/2014 | Stone et al. | |
| 2014/0142576 A1 | 5/2014 | Shipley | |
| 2014/0155895 A1 | 6/2014 | Mcclellan et al. | |
| 2014/0277175 A1 | 9/2014 | Campbell et al. | |
| 2014/0309699 A1 | 10/2014 | Houff | |
| 2015/0066029 A1 | 3/2015 | Zeitani | |
| 2015/0342657 A1 | 12/2015 | Voisard et al. | |
| 2019/0119018 A1 * | 4/2019 | Chmelar ............ | B65D 63/1072 |

FOREIGN PATENT DOCUMENTS

| | | |
|---|---|---|
| WO | WO-2012114360 A1 | 8/2012 |
| WO | WO-2022173651 A1 | 8/2022 |

OTHER PUBLICATIONS

"International Application Serial No. PCT/US2022/015097, Written Opinion mailed May 24, 2022", 9 pgs.

"International Application Serial No. PCT/US2022/015097, International Preliminary Report on Patentability mailed Aug. 24, 2023", 11 pgs.

"Australian Application Serial No. 2022219047, First Examination Report mailed Apr. 24, 2024", 4 pgs.

"Australian Application Serial No. 2022219047, Respone Filed Jul. 4, 2024 to First Examination Report mailed Apr. 24, 2024", 20 pgs.

"Australian Application Serial No. 2022219047, Subsequent Examination Report mailed Jul. 5, 2024", 4 pgs.

"European Application Serial No. 22705304.8, Response Filed Mar. 20, 2024 to Communication pursuant to Rules 161(1) and 162 EPC mailed Sep. 20, 2023", 14 pgs.

* cited by examiner

FIG. 9

# RIGID STERNAL FIXATION

CLAIM OF PRIORITY

This application claims the benefit of U.S. Provisional Patent Application Ser. No. 63/147,409, filed on Feb. 9, 2021, the benefit of priority of which is claimed hereby, and which is incorporated by reference herein in its entirety.

BACKGROUND

A sternotomy is a procedure performed to separate a sternum of a patient to gain access to the breast or chest cavity of the patient, such as for corrective heart procedures. During a sternotomy procedure a vertical (superior to inferior) cut is made through the sternum allowing the sternum to be cracked or separated to provide access to the chest cavity. Following a procedure within the chest cavity, the sternum must be closed. Commonly, sternotomies are closed or repaired using a wire cerclage wrapped around the sternal halves or a rigid bone plate secured to the sternal halves using bone screws.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Sternotomies are often performed on a sternum of a patient (such as prior to a cardiac procedure) by creating a midline resection and separating two halves or portions of the sternum for access to the chest cavity of the patient. Following the procedure, the sternum is often repaired using one or more wire cerclages to hold the two halves in place while the halves heal together. While wire cerclages can help to prevent medial-lateral separation (or relative movement of the halves) of the sternum, wire cerclages are less effective at limiting relative anterior-posterior movement of the halves and are also less effective at limiting relative superior-inferior movement of the halves. Wire cerclages can also unintentionally penetrate outer portions of the sternum. Rigid bone plates are a strategy often used to address the shortcomings of wire cerclages. Rigid bone plates can be secured to each portion or half of the sternum and can help to limit relative movement of the sternal halves in all directions. However, bone plate and screw assemblies can be relatively expensive as compared to wire cerclages and can add a significant number of steps to the repair procedure to properly secure the plate to the sternal halves, as 10 to 20 or more screws are often used to secure the plates.

The inventors have recognized that an anchor assembly can be used to secure the sternal halves to help limit movement of the sternal halves relative to each other while reducing costs with respect to a plate system. The anchor assembly can include an anchor insertable into a bone tunnel between the sternal halves and can include one or more cerclage elements attached to the anchor. The cerclage element(s) can be positioned around the sternal halves and locked to the anchor using a lock, such as an integral ratcheting lock (similar to those used in cable ties). Use of such an anchor assembly to repair a sternotomy can require fewer steps than that of a rigid plate assembly and screw system while use of such an anchor assembly can resist relative movement of the sternal halves better than a wire cerclage.

The above discussion is intended to provide an overview of subject matter of the present patent application. It is not intended to provide an exclusive or exhaustive explanation of the invention. The description below is included to provide further information about the present patent application.

Figure 1:
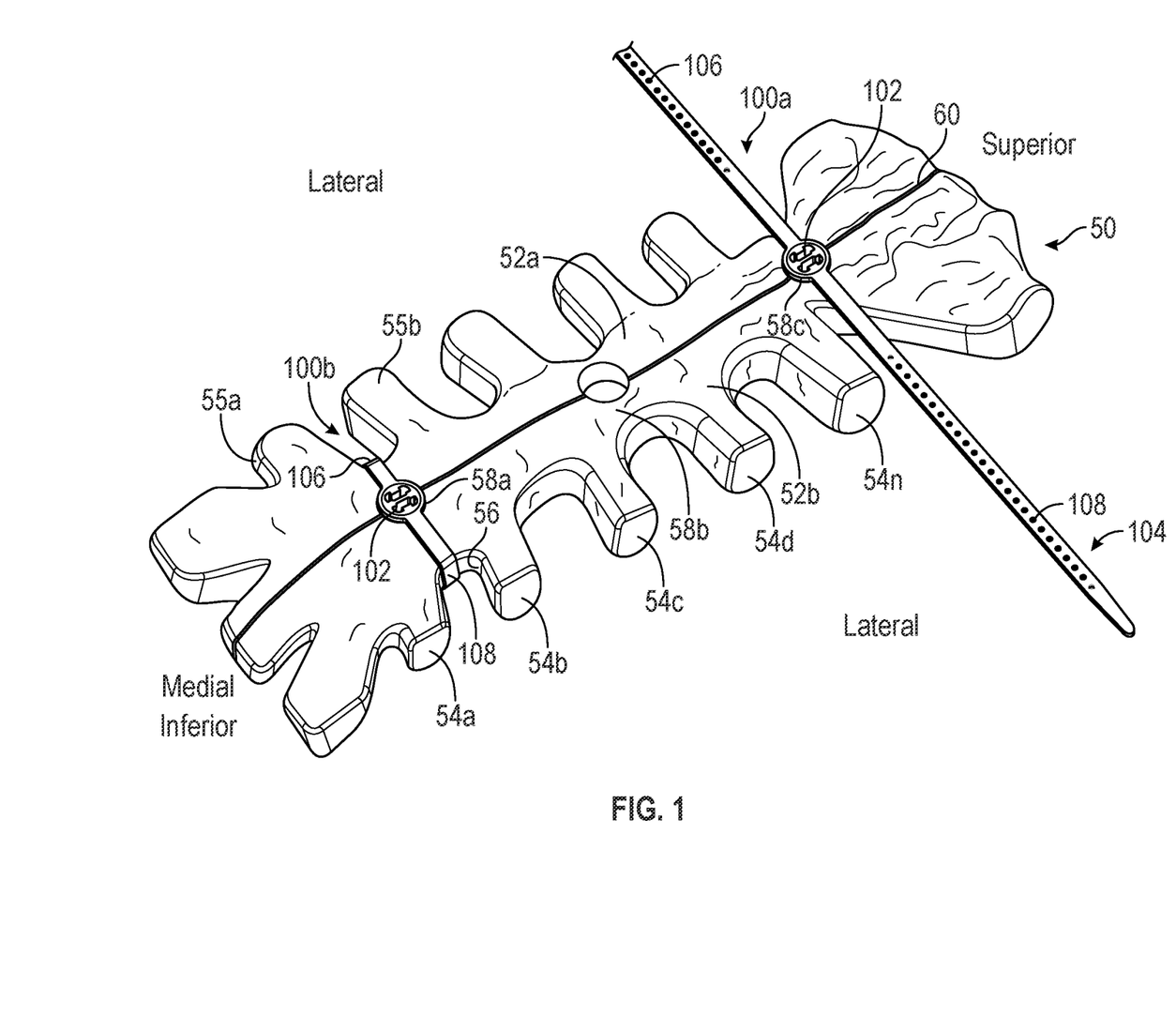
FIG. 1 illustrates an isometric view of a sternum, ribs, and anchor assemblies.

FIG. 1 illustrates an isometric view of a sternum 50, sternal portions 52a and 52b, ribs 54a-54n, ribs 55a-55n, and anchor assemblies 100a and 100b. The anchor assemblies 100a and 100b can each include an anchor 102 and a cerclage 104. The cerclage 104 can include cerclage elements 106 and 108. The cerclage elements 106 and 108 can be connected to the anchor 102 and can extend outward from the body. FIG. 1 also shows orientation indicators Superior, Inferior, Medial, and Lateral.

During a sternotomy, one or more bone tunnel 58 (58a-58c) can be made at the midline 60 of the sternum 50 either before or after the midline cut is performed. In some examples, a cut guide can be used to create the midline cut or the bone tunnels 58. After creation of the bone tunnels 58, the anchor 102 of the anchor assembly 100 can be inserted into the bone tunnel 58. For example, the anchor 102 of the assembly 100A can be inserted into the bone tunnel 58c. Then, the first cerclage element 108 can be positioned between the ribs, such as the ribs 54a and 54b and the cerclage element 108 can be wrapped at least partially around the sternal portion 52b of the sternum 50 before being secured to a lock of the assembly. Then, the cerclage element 106 can be positioned between the ribs such as the ribs 55a and 55b. and can be wrapped at least partially around the sternal portion 52a of the sternum 50 before being secured to the lock.

The cerclage 104 can also be used to approximate the sternal portions by tightening the cerclage elements 106 and 108 and can be used to reduce the sternal portions 52a and 52b by further tightening of the cerclage elements 106 and 108 to the lock (or locks). Because bone tunnels 58 can be created prior to creating the midline resection, positioning of the anchor 102 in the bone tunnels 56 can help to ensure that the sternal halves 52a and 52b are properly positioned together.

Once the sternal portions 52a and 52b are aligned, the cerclage 104 can be tightened using the lock to fix the position of the cerclage 104 with respect to the sternum 50 and the anchor 102, helping to limit movement of the sternal portions 52a and 52b relative to each other in the medial-lateral, superior-inferior, and posterior-anterior directions. The anchor assemblies 100 are discussed in further detail below.

Figure 2A:
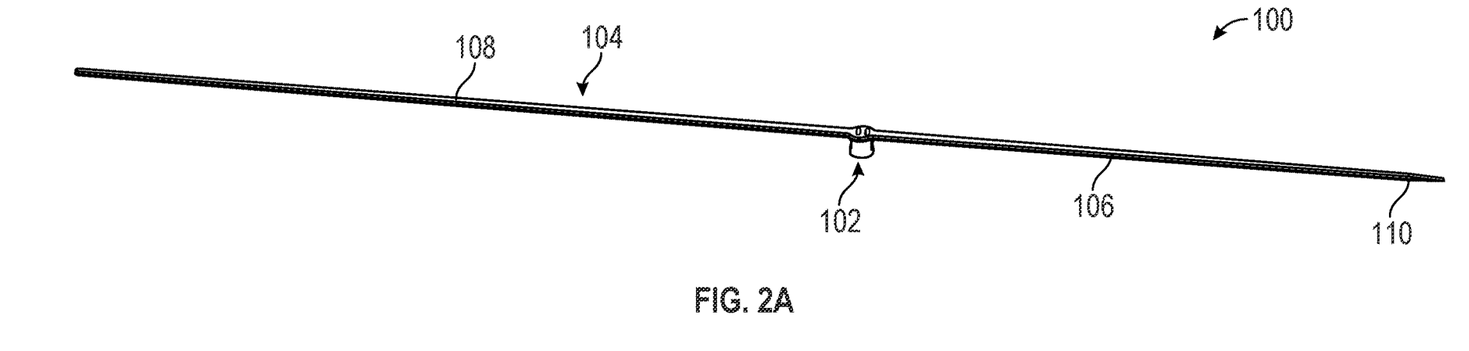
FIG. 2A illustrates an isometric view of an anchor assembly.
Figure 2B:
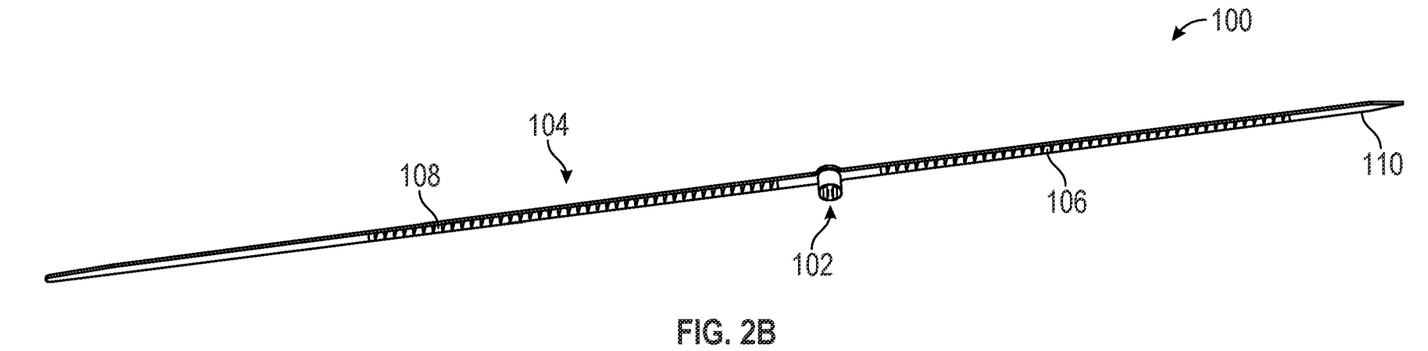
FIG. 2B illustrates an isometric view of an anchor assembly.

FIG. 2A illustrates an isometric view of the anchor assembly 100. FIG. 2B illustrates an isometric view of the anchor assembly 100. FIGS. 2A and 2B are discussed together below. The anchor assembly 100 can be similar to the assemblies 100 of FIG. 1; additional details are discussed below with reference to FIGS. 2A and 2B.

For example, FIGS. 2A and 2B show that the cerclage elements 106 and 108 can be relatively long and can extend outward from the anchor 102. The cerclage elements 106 and 108 can be different lengths. For example, the cerclage element 108 can be longer than the cerclage element 106 such that the cerclage element 108 to allow the cerclage element 108 to be used for approximation and reduction of the sternal portions (such as the portions 52a and 52b of FIG. 1).

The anchor assembly 100 (including the anchor 102 and the cerclage 104) can be made of materials such as metals, plastics, foams, elastomers, ceramics, composites, or combinations thereof. In some examples, anchor assembly 100 can be comprised of biocompatible materials such as such as stainless steels, cobalt-chromium, titanium variations, polyether ether ketone (PEEK), polyether ketone ketone (PEKK), or combinations thereof.

FIGS. 2A and 2B also show that the cerclage 104 can include one or more needles 110. The needle 110 can be connected and end or near an outer end of the cerclage element 106. The needle 110 can be used to more easily pass the cerclage element 106 through costal tissues between ribs. Following passing the cerclage element 106 through costal tissue, the needle 110 can be removed (cut off). The cerclage element 108 can also include a needle.

Figure 3A:
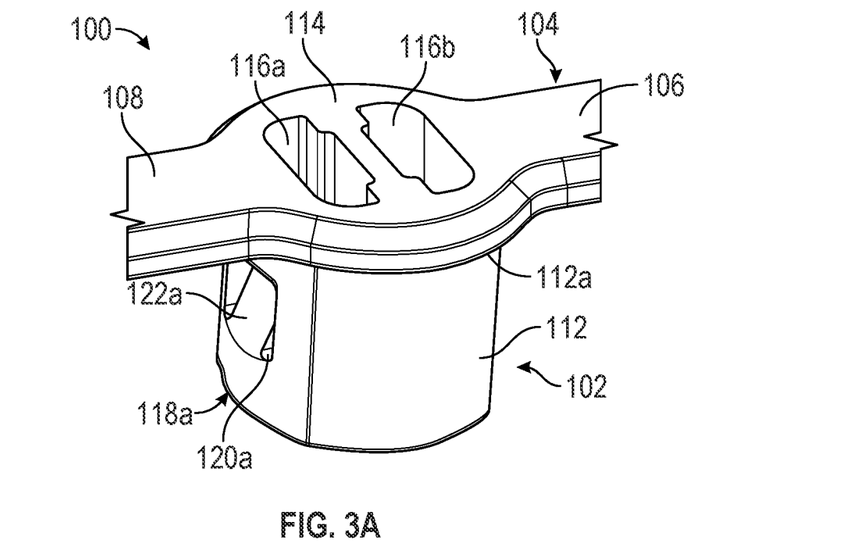
FIG. 3A illustrates an enlarged isometric view of an anchor assembly.
Figure 3B:
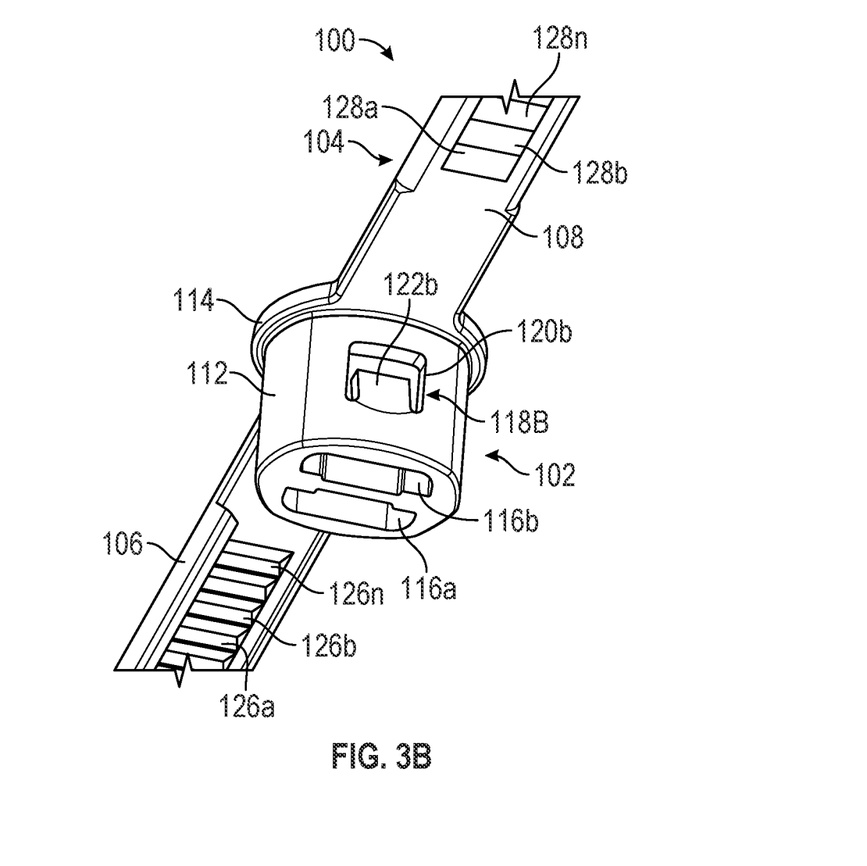
FIG. 3B illustrates an enlarged isometric view of an anchor assembly.
Figure 3C:
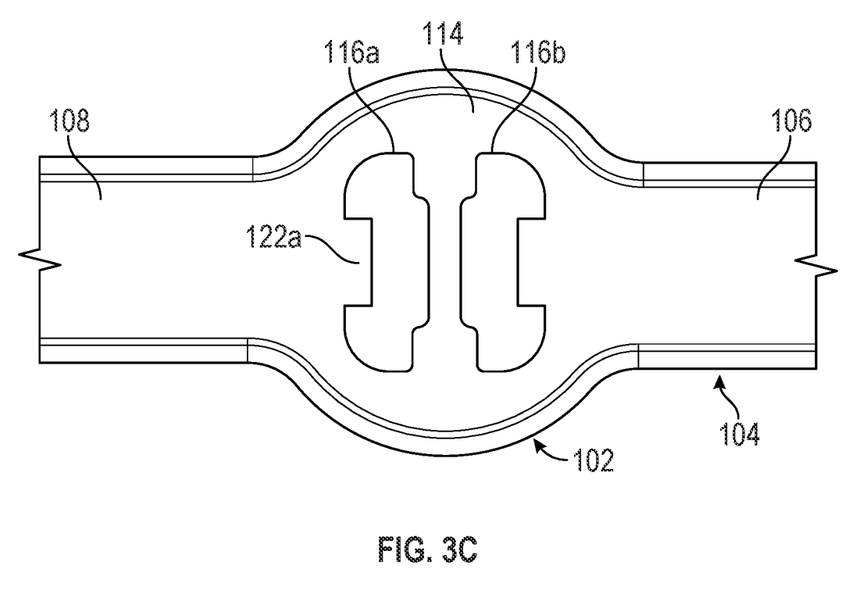
FIG. 3C illustrates an enlarged top view of an anchor assembly.

FIG. 3A illustrates an enlarged isometric view of the anchor assembly 100. FIG. 3B illustrates an enlarged isometric view of the anchor assembly 100. FIG. 3C illustrates an enlarged top view of the anchor assembly 100. The anchor assembly of FIGS. 3A-3C can be similar to the anchor assembly 100 discussed in FIGS. 1-2; additional details are discussed below with reference to FIGS. 3A-3C.

For example, FIGS. 3A and 3B show that the anchor 102 can include a body 112 and a collar 114. The body 112 can be substantially cylindrical and configured to be inserted into a bone tunnel (e.g., the bone tunnels 56 of FIG. 1). The body 112 can be other shapes in other examples such as a cuboid, a hexagonal prism, octagonal prism, or the like. The collar 114 can extend outward (such as radially outward) from an end portion 112a of the body 112 such that the collar 114 has a diameter or radially outer dimension that is larger than that of the body 112. The collar 114 can be configured to engage a top surface of a sternum (such as the sternum 50) when the body 112 is inserted into the bone tunnel (such as the bone tunnel 56) to help limit movement of the anchor 102 into the bone tunnel (posteriorly). Optionally, a second collar can be connected to an end of the body 112 opposite the collar 114 that can extend radially outward therefrom. The second collar and the collar 114 can together capture a sternum therebetween.

The body 112 and the collar 114 (i.e., the anchor 102) can be a rigid or semi-rigid body configured to engage the sternal halves without plastically deforming under loading of normal daily activities. Conversely, the cerclage 104 can be relatively flexible to allow the cerclage to change shapes to conform to the sternal half (or halves) around which the cerclage is positioned.

FIGS. 3A-3C also show that the anchor 102 can include channels 116a and 116b extending through the body 112 and the collar 114. The channels 116a and 116b can be sized to receive the cerclage elements 106 and 108, respectively, therein or therethrough to help allow the cerclage elements 106 and 108 to lock to the anchor 102 to secure the sternal halves or portions. In some examples, the channels 116a and 116b can be the same size and shape in a mirrored configuration. In some examples, the channels 116 can be different sizes, shapes, or orientations.

FIGS. 3A-3C also show that the anchor 102 can include locks 118a and 118b, which can be optionally integrally formed into the body 112 of the anchor 102. The locks 118a and 118b can include slots 120a and 120b, respectively, and ratchets 122a and 122b, respectively. The ratchets 122a and 122b can extend into the slots 120a and 120b, respectively, through other walls of the body 112 such that the ratchets 122a and 122b can extend into the channels 116a and 116b, respectively. By extending into the channels 116a and 116b, respectively, the ratchets 122a and 122b can engage the cerclage elements 108 and 106, respectively, when the cerclage elements 108 and 106 are passed through the channels 116a and 116b, respectively, allowing the cerclage elements 106 and 108 to lock to the body 112.

FIG. 3B also shows teeth 126a-126n of cerclage element 106 and teeth 128a-128n of cerclage element 108. The teeth 126 and 128 can be raised portions on an underside of the cerclage elements 106 and 108, respectively. The teeth 126 and 128 can be configured to engage the ratchets 122a and 122b, respectively to lock the cerclage elements 106 and 108 in their respective positions. Together, the teeth 126 and 128 and the ratchets 122a and 122b can form uni-directional locks, ratcheting mechanisms, or ratcheting locks, which can help to prevent the cerclage elements 106 and 108 from backing out of the locks 118.

When the anchor 102 is implanted, the collar 114 can engage the outer surface (e.g., anterior surface) of the sternum to limit movement of the anchor 102 into the bone tunnel (e.g., bone tunnel 56a). Also, the body 112 can engage the bone tunnel and therefore the sternal halves 52a and 52b to help limit movement relative to each other in the interior and superior directions. When the anchor 102 is secured within the bone tunnel and when the cerclage 104 is secured to the lock 118 (or locks 118a and 118b), the cerclage 104 can help to limit separation of the sternal halves 52a and 52b, or can help to limit relative medial and lateral movement of the sternal halves 52a and 52b. Also, when the anchor 102 is secured within the bone tunnel and when the cerclage 104 is secured to the lock 118 (or locks 118a and 118b), the cerclage 104 can help to limit relative movement of the sternal halves in the anterior and posterior directions. In this way, the anchor assembly can help to limit separation or movement of the sternal halves while helping to reduce costs over other solutions.

Figure 4A:
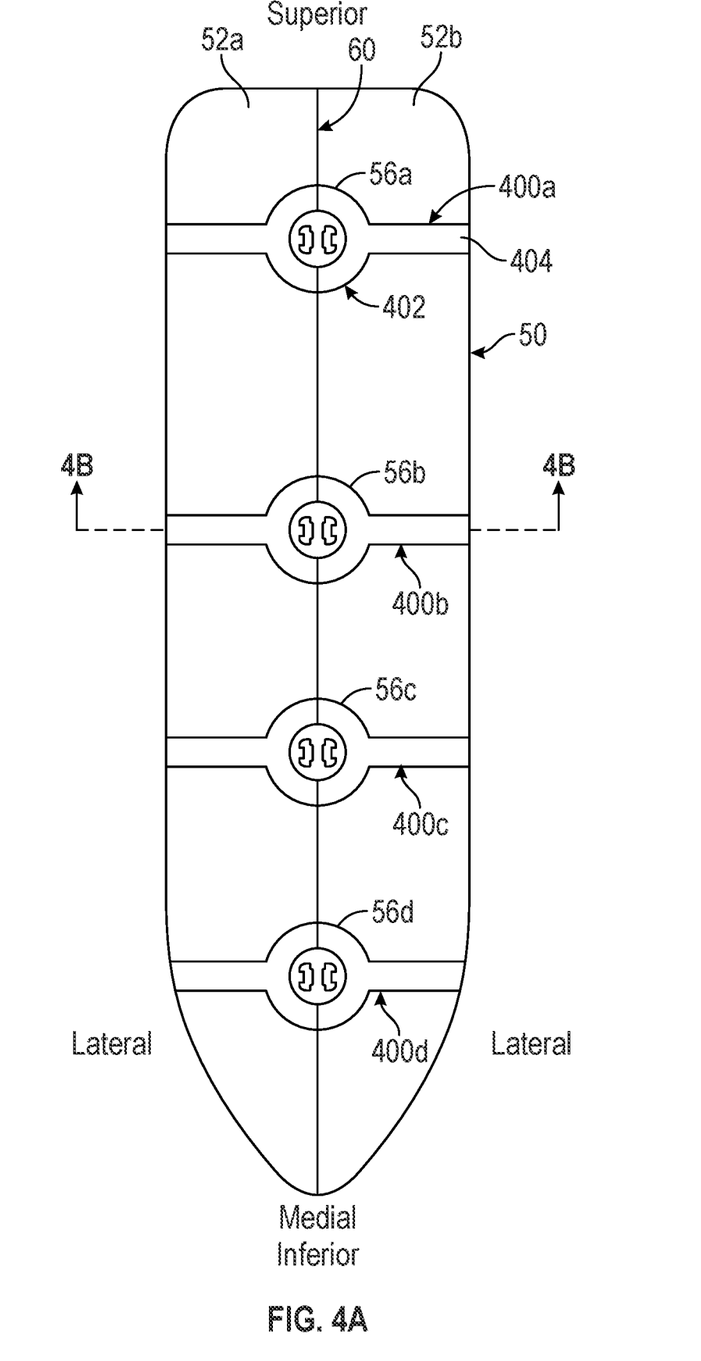
FIG. 4A illustrates a top view of a sternum and anchor assemblies.
Figure 4B:
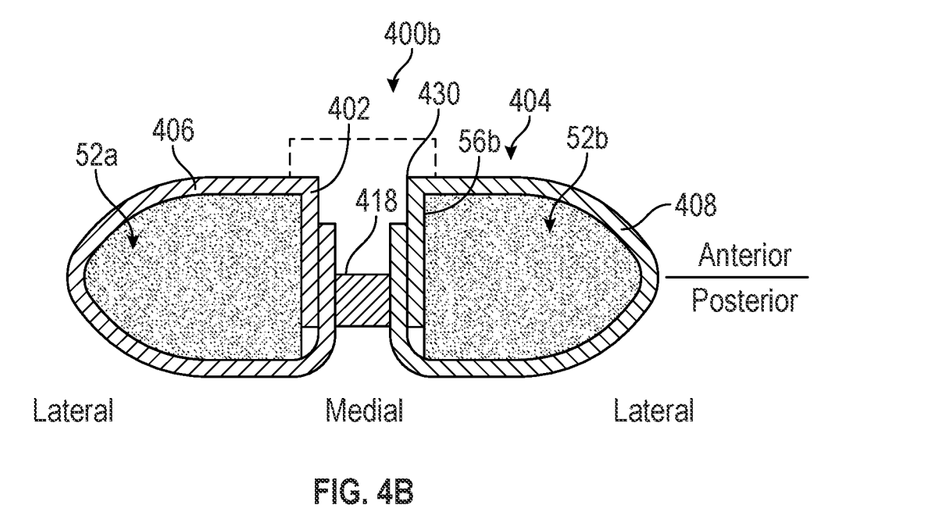
FIG. 4B illustrates a cross-sectional view of a sternum and an anchor assembly.

FIG. 4A illustrates a top view of a sternum 50 and anchor assemblies 400a-400d. FIG. 4B illustrates a cross-sectional view across indicators 4B-4B of FIG. 4A of the sternum and the anchor assembly 400b. FIG. 4A also shows orientation indicators Superior, Inferior, Medial, and Lateral. FIG. 4B also shows orientation indicators Anterior, Posterior, Medial, and Lateral. FIGS. 4A and 4B are discussed together below.

The anchor assemblies 400 can be similar to the anchor assemblies 100 discussed above. The anchor assembly 400 can include an anchor 402 and a cerclage 404 including cerclage elements 406 and 408. The anchor 402 can be positionable in the bone tunnel 56b and the cerclage element 406 can extend around, or at least partially around, the sternal portion 52a and the cerclage element 408 can extend around, or at least partially around, the sternal portion 52b. The cerclage elements 406 and 408 can engage a lock 418 to secure the cerclage elements 406 and 408 to the sternal halves 52a and 52b, respectively. The lock 418 can be a ratcheting lock, such as a cable-tie type lock, or can be other lock types (e.g., fasteners, clamps, adhesives, or the like).

FIG. 4B shows that the anchor assembly 400 can include an opening 430 at an anterior portion of the anchor 402, which can provide access to the cerclage elements 406 and 408 near the lock 418. The opening 430 can thereby allow for the cerclage elements 406 and 408 to be trimmed near the lock 418, posteriorly of the anterior surface of the anchor 402, which can help to reduce palpability of the anchor assembly 400 and can help to limit tissue interaction between the cut ends of the cerclage 404 and tissues (e.g., skin).

Figure 5A:
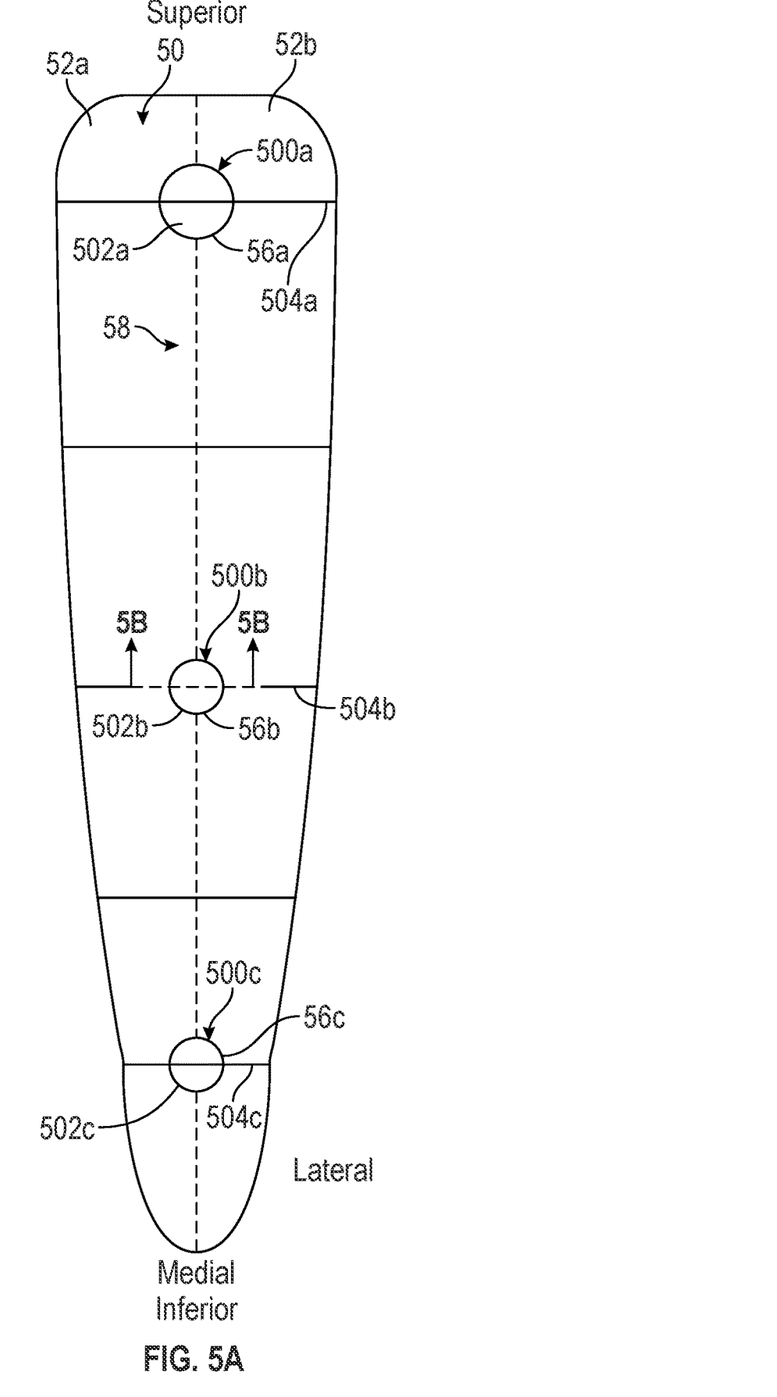
FIG. 5A illustrates a top view of a sternum and anchor assemblies.
Figure 5B:
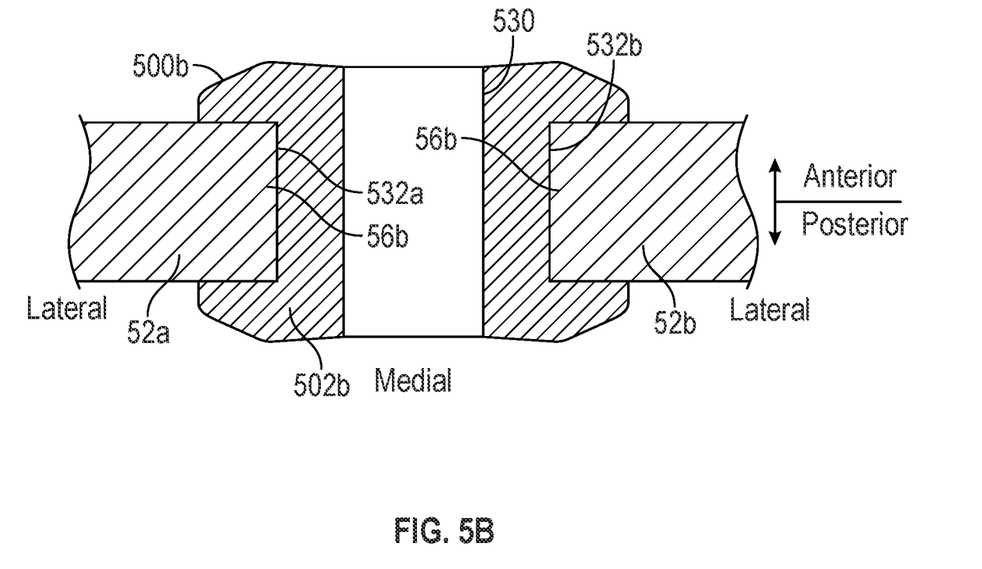
FIG. 5B illustrates a cross-sectional view of a sternum and an anchor assembly.

FIG. 5A illustrates a top view of a sternum 50 and anchor assemblies 500a-500c. FIG. 5B illustrates a cross-sectional view across indicators 5B-5B of FIG. 5A of the sternum and the anchor assembly 500b. FIG. 5A also shows orientation indicators Superior, Inferior, Medial, and Lateral. FIG. 5B also shows orientation indicators Anterior, Posterior, Medial, and Lateral. FIGS. 5A and 5B are discussed together below.

The anchor assemblies 500 can be similar to the anchor assemblies 100 and 400 discussed above in that they include an anchor 502. The anchor 500 can include a body 502 or button that can be positionable in the bone tunnel 56b. The body 502 can also include slots 532a and 532b which can extend radially inward from a radially (laterally) outer surface of the body 502. The slots 532a and 532b can be one slot extending around a circumference of the body 502 or can be individual or discreet slots. The slots 532 can be notches, undercuts, channels, or the like.

The slots 532a and 532b can be configured to receive the sternal halves 52a and 52b at the bone tunnel 56b, as shown in FIG. 5B. When the sternal halves 52a and 52b are positioned in the slots, engagement between flanges defining the slots 532 and between the sternal halves 52 can help to limit relative anterior and posterior movement of the sternal halves 52a and 52b. For example, engagement between the sternal halves 52a and 52b and the slots 532a and 532b, respectively, can help to limit anterior and posterior movement of the sternal halves 52a and 52b with respect to each other.

In examples where the slots 532 extend to superior and inferior portions of the body 502, the slots 532 can also help to limit relative inferior and superior movement of the sternal portions 502a and 502b. Any of the anchor assemblies discussed above or below can be modified to include the slots of the anchor assembly 500.

The assembly 500 can also include a cerclage 504 which can be a cable-tie type cerclage, as discussed in the assemblies above, or can be other types of cerclages. For example, wire can be used with the anchor 500, as the wire can be fed through the opening 530 in the body 502. Similarly, a cable tie-type cerclage can be fed through the opening 530. Optionally, the opening 530 can be capped or filled. Use of any type of cerclages can help to limit movement of the sternal halves 52 relative to each other in medial and lateral directions.

Optionally, a single cerclage element can be used to pass around the sternal halves 52a and 52b without passing through the opening 530. In such an example, the body can help to limit movement of the sternal halves 52 in the anterior and posterior directions.

In use, the assemblies 500 can be secured to one sternal half (e.g., 52b) using the slot 532b and then the other sternal half 52a can be moved into the slots 532a to approximate the sternal anteriorly-posteriorly and superiorly-inferiorly. The cerclage 504 can then be placed to approximate medially-laterally and to secure the assemblies 500 in place with respect to the sternum 50. Optionally, ends of the cerclage can be positioned in the opening 530, which can be optionally capped. The diameter or size of the channels 532 can be optionally sized for creation of the bone tunnels 56 prior to resection of the midline 58. That is, bone material may be removed during the midline 58 resection, changing the shape of the bone tunnels 56. The channels 532 can be sized to accommodate the change in shape or in size of the bone tunnels 56.

Figure 6:
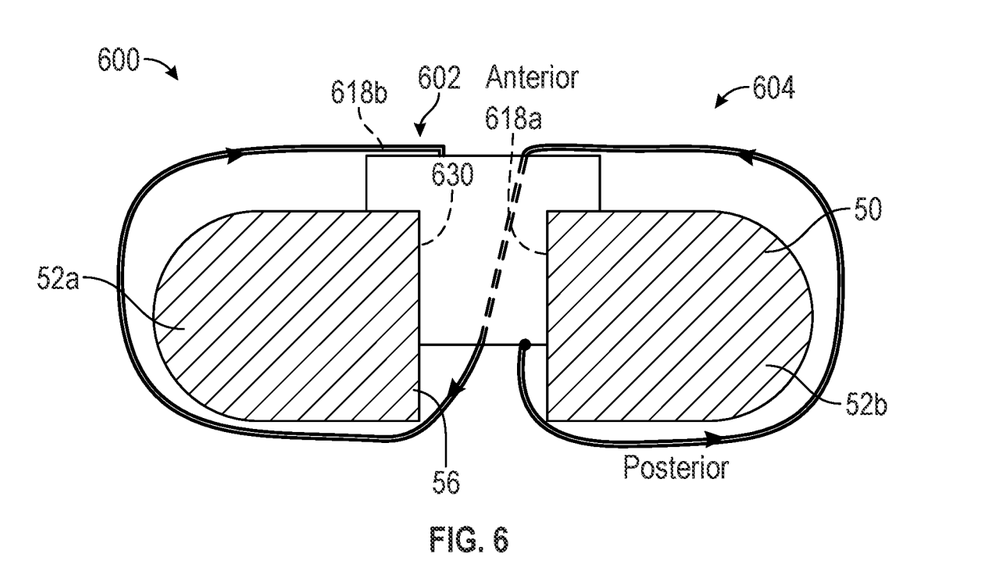
FIG. 6 illustrates a cross-sectional view of a sternum and an anchor assembly.

FIG. 6 illustrates a cross-sectional view of a sternum 50 and an anchor assembly 600. FIG. 6 also shows orientation indicators Anterior and Posterior. The anchor assembly 600 can be similar to those discussed above, such as the anchor assembly 100; the assembly 600 can differ in that the cerclage 604 can include a single cerclage element.

The cerclage 604 can be connected to the anchor 602, such as at a posterior portion of the anchor 602. In use, the cerclage 604 can be wrapped around the sternal portion 52b and then passed through an opening 630 of the anchor 602. Optionally, the anchor 602 can include a first lock 618a in the opening 630 that can allow the cerclage 604 to be secured around the sternal portion 52b and then locked to the anchor 602. Once the cerclage 604 is secured to the first lock 618a (or optionally after passing through the opening 630), the cerclage 604 can be passed around the sternal portion 52a and can be secured to the anchor 602 by a second lock 618b. The second lock 618b can be in other locations in other examples.

In some examples, the anchor 602 and the cerclage 604 can be integrally formed or can be a single piece. The use of a single-piece assembly or a single cerclage element can help to simplify approximation and reduction of the two sternal halves.

Figure 7:
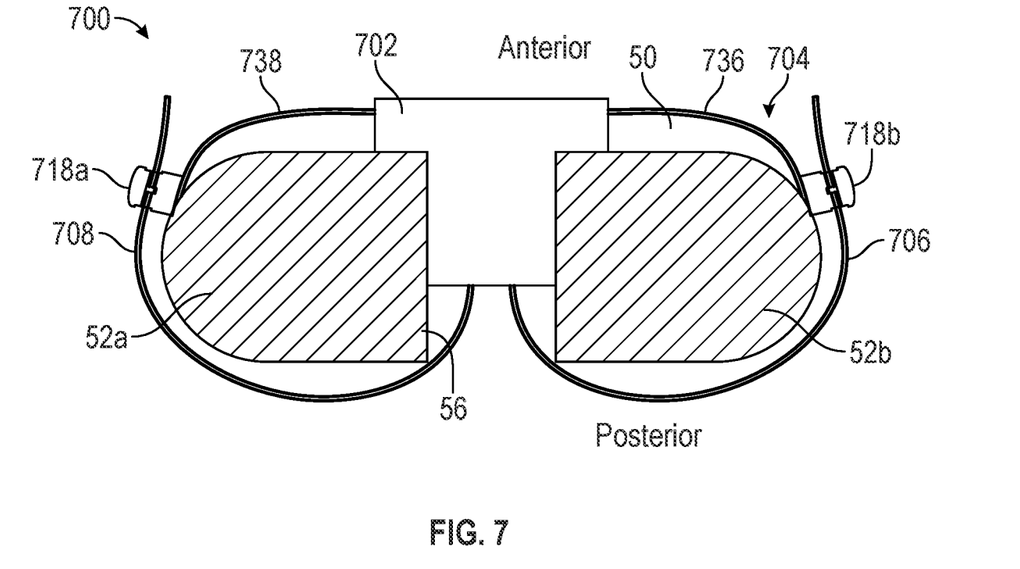
FIG. 7 illustrates a cross-sectional view of a sternum and an anchor assembly.

FIG. 7 illustrates a cross-sectional view of a sternum 50 and an anchor assembly 700. FIG. 7 also shows orientation indicators Anterior and Posterior. The anchor assembly 700 can be similar to those discussed above, such as the anchor assembly 100, the assembly 700 can differ in that a cerclage 704 can include four elements, 706, 708, 736, and 738.

The cerclage elements 706 and 708 can extend from posterior portions of the anchor 702 such that the cerclage element 708 can be positioned at least partially around the sternal half 52a and the cerclage element 706 can extend at least partially around the cerclage half 52b. The cerclage element 738 can extend from an anterior portion of the anchor 702 around the sternal half 52a where the cerclage element 738 can connect to a lock 718a configured to receive the cerclage element 708 to secure the cerclage elements 708 and 738 around the sternal half 52a. Similarly, the cerclage element 736 can extend from an anterior portion of the anchor 702 around the sternal half 52b where the cerclage element 736 can connect to a lock 718b configured to receive the cerclage element 706 to secure the cerclage elements 706 and 736 around the sternal half 52b.

By locating the locks 718 outside of the anchor 702, the anchor 702 can have a relatively smaller diameter or size, which can allow the bone tunnel 56 to be relatively smaller, which can help to improve patient healing. The locks 718 can be located anywhere along any of the cerclage elements 706, 708, 736, and 738

Figure 8A:
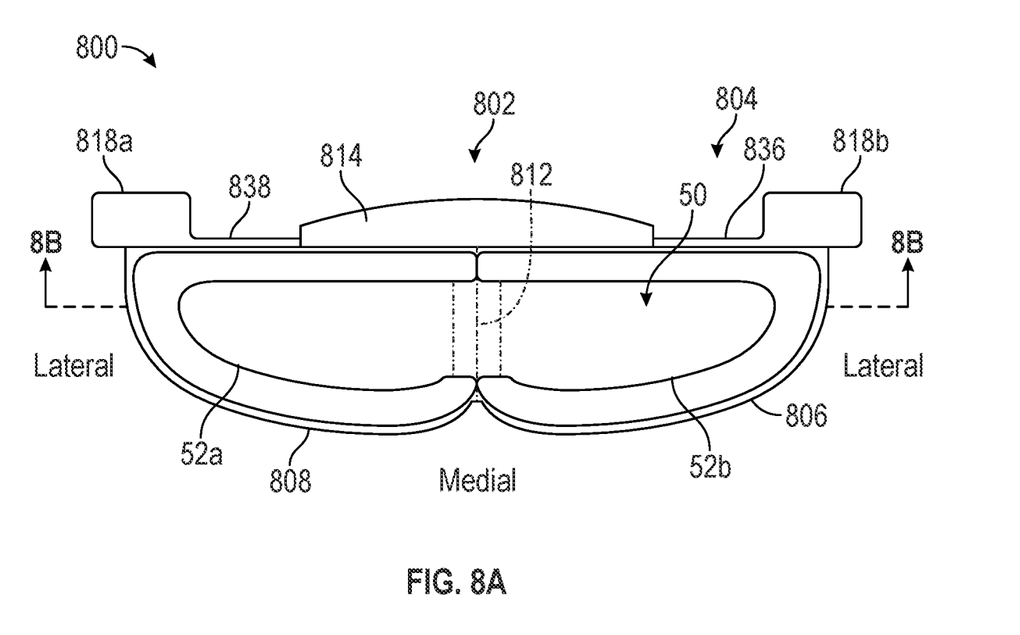
FIG. 8A illustrates a cross-sectional view of a sternum and an anchor assembly.
Figure 8B:
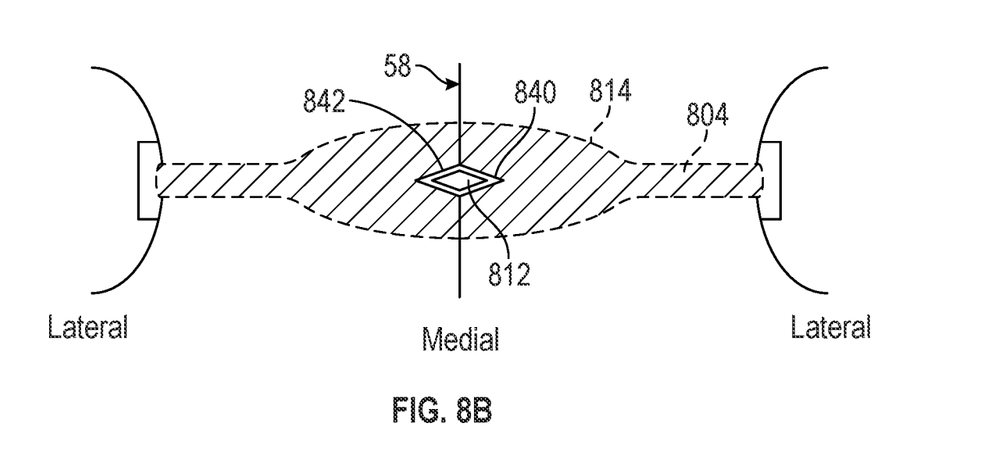
FIG. 8B illustrates a cross-sectional view across indicators 8B-8B of FIG. 8A of a sternum and an anchor assembly.

FIG. 8A illustrates a cross-sectional view of a sternum 50 and an anchor assembly 800. FIG. 8B illustrates a cross-sectional view across indicators 8B-8B of FIG. 8A of the sternum 50 and the anchor assembly 800. FIGS. 8A and 8B also show orientation indicators medial and lateral. FIGS. 8A and 8B are discussed together below.

The anchor assembly 800 can include an anchor 802 and a cerclage 804. The anchor 802 can include a body 812 and a collar 814. The cerclage 804 can include cerclage elements, 806, 808, 836, and 38. The anchor assembly 800 can also include locks 818a and 818b. The anchor assembly 800 can be similar to the anchor assemblies discussed above; anchor assembly 800 can differ in that it can have a body with a diamond shape. Any of the anchor assembles discussed above can be modified to include a body with a similar shape.

The body 812 can be shaped similar to that of a diamond from a posterior direction, as shown in FIG. 8B. That is, the body 812 can include projections 840 and 842 extending outward (e.g., laterally) from the body 812, which can terminate in a point such that the projections 840 and 842 are relatively sharp. In operation, the sharp projections can engage the sternal halves 52a and 52b when the halves 52 are reduced to engage each other and to engage the projections 840 and 842. Because the sternal halves have already been cut at the midline 58, relatively soft bone of the sternal halves will engage the projections 840 and 842 during reduction such that the projections 840 and 842 can penetrate or deform the bone of the sternal halves 52a and 52b to create a bone tunnel for the body 812 in the sternal halves 52a and 52b without a drilling operation. Such a body can be thereby installed without a drilling operation, which can save time during a procedure to close a sternotomy. Optionally, the projections 840 and 842 can include multiple points or can include serrations.

Figure 9:
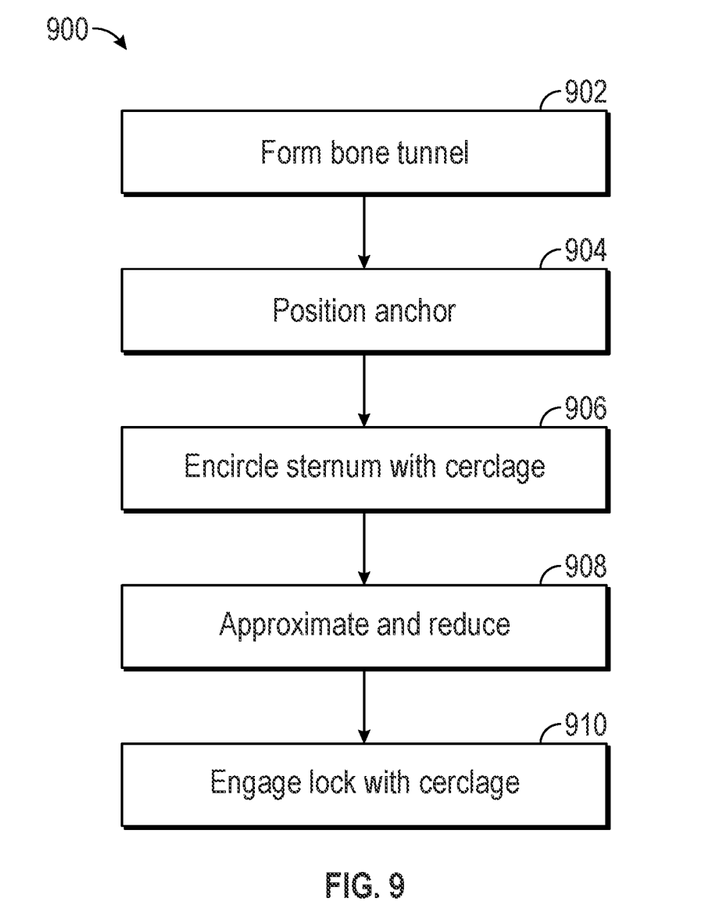
FIG. 9 illustrates a schematic view of a method.

FIG. 9 illustrates a schematic view of the method 900, in accordance with at least one example of this disclosure. The method 900 can be a method of repairing a sternotomy using an anchor assembly. More specific examples of the method 900 are discussed below. The steps or operations of the method 900 are illustrated in a particular order for convenience and clarity; many of the discussed operations can be performed in a different sequence or in parallel without materially impacting other operations. The method 900 as discussed includes operations performed by multiple different actors, devices, and/or systems. It is understood that subsets of the operations discussed in the method 900 can be attributable to a single actor, device, or system could be considered a separate standalone process or method.

The method 900 can begin with performing a sternotomy, such as making an incision and making a superior-to-inferior cut through a sternum. The method can begin or continue at step 902 where a bone tunnel can be created along the midline of a sternum, where the bone tunnel can be formed in a first portion of the sternum and a second portion of the sternum. For example, the bone tunnel 56 can be created along the midline 58 of the sternum 50. At step 904, an anchor of an anchor assembly can be positioned along the midline between the first portion of the sternum and the second portion of the sternum. For example, the anchor 102 can be positioned along the midline 58 between the first and second portions 52a and 52b.

At step 906, at least a portion of the first portion of the sternum can be encircled with a cerclage of the anchor assembly, where the cerclage can be connected to the anchor and at least a portion of the second portion of the sternum can be encircled with the cerclage of the anchor. For example, the portion 52a can be at least partially encircled by the cerclage 104 (e.g., 106, 108), which can be connected to the body, and the portion 52b can be encircled by the cerclage 104. At step 908, the first sternum portion and the second sternum portion can be approximated using the cerclage. For example, the sternal portions 52a and 52b can be approximated using the cerclage 104, such as after the cerclage 104 is at least partially surrounding the sternal portion 52a. Also, at step 908, the first sternum portion and the second sternum portion can be reduced by tightening the cerclage in the lock. For example, the sternal portions 52a and 52b can be reduced by tightening the cerclage 104 in the lock 118.

At step 910, a lock of the anchor assembly can be engaged with the cerclage to secure the cerclage to the lock and to the anchor of the anchor and to secure the first portion of the sternum to the second portion of the sternum. For example, the lock 118 can be engage with the cerclage 104 to secure the cerclage 104 to the lock 118.

In another example the cerclage 104 can be passed through the anchor 102 after encircling the portion of the first portion of the sternum 52a and before encircling the portion of the second portion of the sternum 52b. In another example, a cut guide can be used to perform the sternotomy along the midline 58 and through a center of the bone tunnel 56, wherein the bone tunnel 56 can be formed using the cut guide. In another example, the cut guide can be used to perform the sternotomy along the midline 58 and through a center of the bone tunnel, where the bone tunnel 56 can be formed using the cut guide.

In another example, the needle 110 of the cerclage 104 can be passed through intercostal space and the needle 110 can be removed from the cerclage 104 after passing at least a portion of the cerclage 104 through the intercostal space.

In another example, at least the portion of the first portion 52b of the sternum can be encircled with a first element 108 of the cerclage 104 and at least a portion of the second portion 52a can be at least partially encircled by a second element 106 of the cerclage 104, where the first element 108 and the second element 106 can be connected to the anchor 102.

In another example, the lock 118 can include a first lock 118a can engage with the first element 108 of the cerclage 104 and can include a second lock 118b of engageable with the second element 106 of the cerclage. Optionally, the first lock 118a and the second lock 118b can be integrally formed with the anchor 102.

NOTES AND EXAMPLES

The following, non-limiting examples, detail certain aspects of the present subject matter to solve the challenges and provide the benefits discussed herein, among others.

Example 1 is an anchor assembly for securing a first portion and a second portion of a separated sternum, the anchor assembly comprising: a lock; an anchor comprising: a body locatable between the first portion and the second portion of the sternum, the body defining an end portion; and a collar connected to the body and extending outward from the end portion of the body, the collar engageable with an outer surface of the sternum to limit movement of the body beyond the outer surface of the sternum; and a cerclage connected to and extending from the anchor, the cerclage configured to surround at least at least partially surround the first portion and the second portion of the separated sternum, and the cerclage connectable to the lock to secure the cerclage and the anchor to the sternum and to secure the first portion of the separated sternum to the second portion of the separated sternum.

In Example 2, the subject matter of Example 1 optionally includes wherein the cerclage includes a first element and a second element, the first element configured to at least partially surround the first portion of the sternum and the second element configured to at least partially surround the second portion of the sternum.

In Example 3, the subject matter of Example 2 optionally includes wherein the lock includes: a first lock configured to engage the first cerclage to limit movement of the first cerclage element relative to the anchor; and a second lock configured to engage the second cerclage to limit movement of the second cerclage element relative to the anchor.

In Example 4, the subject matter of Example 3 optionally includes wherein the first lock and the second lock include uni-directional ratchet mechanisms.

In Example 5, the subject matter of Example 4 optionally includes wherein the first lock and the second lock are integral to the body of the anchor.

In Example 6, the subject matter of any one or more of Examples 4-5 optionally include wherein the first lock and the second lock are integral to the first element and the second element.

In Example 7, the subject matter of any one or more of Examples 2-6 optionally include wherein the cerclage includes a third element extending from the body, the third element including a first lock of the lock, the first lock configured to secure the first element to the body, and wherein the cerclage includes a fourth element extending from the body, the fourth element including a second lock of the lock, the second lock configured to secure the second element to the body.

In Example 8, the subject matter of any one or more of Examples 1-7 optionally include wherein the body is insertable into a bone tunnel formed in the first portion and the second portion of the sternum, the collar engageable with the outer surface of the sternum to limit movement of the body into the bone tunnel, and the body engageable with the bone tunnel to limit relative movement between the first portion of the sternum and the second portion of the sternum.

In Example 9, the subject matter of any one or more of Examples 1-8 optionally include wherein the body forms a projection engageable with the sternum to form a bone tunnel in the first portion of the sternum.

In Example 10, the subject matter of any one or more of Examples 1-9 optionally include wherein the cerclage is configured to at least partially surround the first portion of the sternum, pass through the body of the anchor, and at least partially surround the second portion of the sternum.

In Example 11, the subject matter of any one or more of Examples 1-10 optionally include wherein the cerclage, the anchor, and the lock are integrally formed.

Example 12 is a method for repairing a midline sternotomy, the method comprising: creating a bone tunnel along the midline of a sternum, the bone tunnel formed in a first portion of the sternum and a second portion of the sternum; positioning an anchor of an anchor assembly along the midline between the first portion of the sternum and the second portion of the sternum; encircling at least a portion of the first portion of the sternum with a cerclage of the anchor assembly, the cerclage connected to the anchor; encircling at least a portion of the second portion of the sternum with the cerclage of the anchor; and engaging a lock of the anchor assembly with the cerclage to secure the cerclage to the lock and to the anchor of the anchor and to secure the first portion of the sternum to the second portion of the sternum.

In Example 13, the subject matter of Example 12 optionally includes approximating the first sternum portion and the second sternum portion using the cerclage.

In Example 14, the subject matter of any one or more of Examples 12-13 optionally include reducing the first sternum portion and the second sternum portion by tightening the cerclage in the lock.

In Example 15, the subject matter of any one or more of Examples 12-14 optionally include passing the cerclage through the anchor after encircling the portion of the first portion of the sternum and before encircling the portion of the second portion of the sternum.

In Example 16, the subject matter of any one or more of Examples 12-15 optionally include using a cut guide to perform the sternotomy along the midline and through a center of the bone tunnel.

In Example 17, the subject matter of Example 16 optionally includes wherein the bone tunnel is formed using the cut guide.

In Example 18, the subject matter of any one or more of Examples 12-17 optionally include passing a needle of the cerclage through intercostal space; and removing the needle from the cerclage after passing at least a portion of the cerclage through the intercostal space.

In Example 19, the subject matter of any one or more of Examples 12-18 optionally include wherein encircling at least the portion of the first portion of the sternum includes encircling the portion with a first element of the cerclage and wherein encircling at least the portion of the second portion of the sternum includes encircling the portion with a second element of the cerclage, the first element and the second element connected to the anchor.

In Example 20, the subject matter of Example 19 optionally includes wherein engaging the lock includes engaging a first lock of the lock with the first element of the cerclage and includes engaging a second lock of the lock with the second element of the cerclage.

In Example 21, the subject matter of Example 20 optionally includes wherein the first lock and the second lock are integrally formed with the anchor.

Example 22 is an anchor assembly for securing a first portion and a second portion of a separated sternum, the anchor assembly comprising: an anchor comprising: a body locatable between the first portion and the second portion of the sternum, the body defining an end portion; and a collar connected to the body and extending outward from the end portion of the body, the collar engageable with an outer surface of the sternum to limit movement of the body beyond the outer surface of the sternum; and a cerclage connected to and extending from the anchor, the cerclage configured to surround at least at least partially surround the first portion and the second portion of the separated sternum, and the cerclage connectable to itself or the anchor to secure the cerclage and the anchor to the sternum and to secure the first portion of the separated sternum to the second portion of the separated sternum.

In Example 23, the apparatuses or method of any one or any combination of Examples 1-22 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An anchor assembly for securing a first portion and a second portion of a separated sternum, the anchor assembly comprising:
    an anchor comprising:
        a body insertable into a bone tunnel of one or more of the first portion and the second portion of the sternum, the body defining an end portion, and the body defining a first channel and a second channel extending through the body; and
        a collar connected to the body and extending laterally outward from the end portion of the body, the collar engageable with an outer surface of the sternum;
        a first lock integral to the body and extending from an outer surface of the body into the first channel and a second lock integral to the body and extending from the outer surface of the body into the second channel; and
    a cerclage integrally formed into and extending from the anchor, the cerclage including a first element configured to at least partially surround the first portion of the separated sternum and insertable through the first channel, the cerclage including a second element configured to at least partially surround the second portion of the separated sternum and insertable through the second channel, and the first element connectable to the first lock and the second element connectable to the second lock to secure the cerclage and the anchor to the sternum and to secure the first portion of the separated sternum to the second portion of the separated sternum.

2. The anchor assembly of claim 1, wherein the first lock is configured to engage the first cerclage element to limit movement of the first cerclage element relative to the anchor, and wherein the second lock is configured to engage the second cerclage element to limit movement of the second cerclage element relative to the anchor.

3. The anchor assembly of claim 2, wherein the first lock and the second lock include uni-directional ratchet mechanisms.

4. The anchor assembly of claim 1, wherein the collar is engageable with the outer surface of the sternum to limit movement of the body into the bone tunnel, and the body is engageable with the bone tunnel to limit relative movement between the first portion of the sternum and the second portion of the sternum.

5. The anchor assembly of claim 1, wherein the body forms a projection engageable with the sternum to form a bone tunnel in the first portion of the sternum.

6. The anchor assembly of claim 1, wherein the cerclage is configured to at least partially surround the first portion of the sternum, pass through the body of the anchor, and at least partially surround the second portion of the sternum.

7. An anchor assembly for securing a first portion and a second portion of a separated sternum, the anchor assembly comprising:
    an anchor comprising:
        a body locatable in a bone tunnel of one or more of the first portion and the second portion of the sternum and locatable between the first portion and the second portion of the sternum, the body including an end portion, the body defining a first bore and a second bore each extending through a top portion and a bottom portion of the body, the body including a first lock integral to the body and extending at least partially into the first bore, and the body including a second lock integral to the body and extending at least partially into the second bore, wherein the body has a cylindrical shape configured for insertion into the bone tunnel, and wherein the first lock and the second lock extend from an outer surface of the body into openings of an outer wall of the body; and
        a collar connected to and extending laterally outward from the end portion of the body, the collar engageable with an outer surface of the sternum to limit movement of the body into the bone tunnel; and
    a cerclage integrally formed with the anchor, the cerclage including a first element configured to at least partially surround the first portion of the separated sternum, the cerclage including a second element configured to at least partially surround the second portion of the separated sternum, and the first portion insertable at least partially into the first bore to engage the first lock to secure the first element to the anchor, and the second portion insertable at least partially into the second bore to engage the second lock to secure the second element to the anchor and to secure the cerclage and the anchor the sternum and to secure the first portion of the separated sternum to the second portion of the separated sternum.

8. The anchor assembly of claim 7, wherein the collar has a diameter that is larger than a diameter of the body.

9. The anchor assembly of claim 7, wherein the first lock and the second lock extend from an outer surface of the body into the first bore and the second bore, respectively.

10. The anchor assembly of claim 7, wherein the collar is configured to engage a top surface of the sternum when the body is inserted into the bone tunnel to limit movement of the anchor into the bone tunnel.

11. The anchor assembly of claim 7, wherein the body forms a projection engageable with the sternum to form a bone tunnel in the first portion of the sternum.

12. The anchor assembly of claim 7, wherein the first lock and the second lock extend from an outer surface of the body into openings of an outer wall of the body.

* * * * *